(12) United States Patent
Abdi et al.

(10) Patent No.: US 11,619,618 B2
(45) Date of Patent: Apr. 4, 2023

(54) SENSOR TUNING—SENSOR SPECIFIC SELECTION FOR IOT—ELECTRONIC NOSE APPLICATION USING GRADIENT BOOSTING DECISION TREES

(71) Applicant: International Business Machines Corporation, Armonk, NY (US)

(72) Inventors: Mohammed Abdi, San Jose, CA (US); Aminat Adebiyi, San Jose, CA (US); Alberto Mannari, San Jose, CA (US); Andrea Fasoli, San Jose, CA (US); Ronald Robert Labby, San Jose, CA (US); Luisa Bozano, Los Gatos, CA (US); Pawan Chowdhary, San Jose, CA (US); Abubeker Abdullahi, Central, SC (US)

(73) Assignee: International Business Machines Corporation, Armonk, NY (US)

( * ) Notice: Subject to any disclaimer, the term of this patent is extended or adjusted under 35 U.S.C. 154(b) by 651 days.

(21) Appl. No.: 16/707,679

(22) Filed: Dec. 9, 2019

(65) Prior Publication Data

US 2021/0172918 A1    Jun. 10, 2021

(51) Int. Cl.
*G01N 33/00* (2006.01)
*G06K 9/00* (2022.01)
(Continued)

(52) U.S. Cl.
CPC ..... *G01N 33/0031* (2013.01); *G06K 9/00523* (2013.01); *G06K 9/623* (2013.01);
(Continued)

(58) Field of Classification Search
CPC ............... G01N 33/0031; G06K 9/623; G06K 9/00523; G16Y 20/10; G16Y 40/35; G16Y 40/10; G06N 20/20
See application file for complete search history.

(56) References Cited

U.S. PATENT DOCUMENTS

| 5,299,118 A | 3/1994 | Martens et al. |
| 7,477,993 B2 * | 1/2009 | Sunshine ............... B82Y 15/00 |
| | | 702/30 |

(Continued)

FOREIGN PATENT DOCUMENTS

| CN | 102512158 A | 6/2012 |
| CN | 103942526 A | 7/2014 |

(Continued)

OTHER PUBLICATIONS

International Search Report for counterpart PCT Application No. PCT/IB2020/061434 dated Mar. 15, 2021.
(Continued)

*Primary Examiner* — Abdullahi E Salad
(74) *Attorney, Agent, or Firm* — Karen Canaan; CanaanLaw, P.C.

(57) ABSTRACT

Provided is a system and method for tuning an array of sensors to enable selection of the most suitable sensors for a target application. After extracting features from sensor raw data, the extracted features are ranked with gradient boosting decision trees to assign an importance value to each extracted feature. A threshold value for the entire set of extracted features is calculated and an importance score is calculated for the individual sensors of the array. Individual sensors with an importance score on or above the threshold value are selected for the target application.

25 Claims, 11 Drawing Sheets

(51) Int. Cl.
G06K 9/62 (2022.01)
G16Y 20/10 (2020.01)
G16Y 40/35 (2020.01)
G16Y 40/10 (2020.01)
G06N 20/20 (2019.01)

(52) U.S. Cl.
CPC .............. *G06N 20/20* (2019.01); *G16Y 20/10* (2020.01); *G16Y 40/10* (2020.01); *G16Y 40/35* (2020.01)

(56) References Cited

U.S. PATENT DOCUMENTS

| | | | |
|---|---|---|---|
| 9,939,412 | B2 | 4/2018 | Ichimura et al. |
| 2003/0068097 | A1 | 4/2003 | Wilson et al. |
| 2005/0216426 | A1* | 9/2005 | Weston ................ G06K 9/6231 706/12 |
| 2007/0028667 | A1 | 2/2007 | Kim et al. |
| 2010/0125417 | A1 | 5/2010 | Hyde et al. |
| 2011/0008212 | A1 | 1/2011 | Ichimura |
| 2017/0293606 | A1* | 10/2017 | Xu ............................ G06N 5/04 |
| 2018/0039906 | A1* | 2/2018 | Bhatt ...................... G06N 20/00 |
| 2019/0101501 | A1 | 4/2019 | Sahu et al. |
| 2019/0111569 | A1 | 4/2019 | Chang et al. |
| 2019/0117964 | A1 | 4/2019 | Bahrami et al. |
| 2019/0317079 | A1* | 10/2019 | Trenholm .............. G16C 20/70 |
| 2020/0160178 | A1* | 5/2020 | Kar ....................... G06K 9/6256 |
| 2020/0210854 | A1* | 7/2020 | Srinivasan ............... G06N 3/08 |
| 2021/0188541 | A1* | 6/2021 | Kurani ...................... B65F 1/14 |

FOREIGN PATENT DOCUMENTS

| | | |
|---|---|---|
| CN | 106716063 A | 5/2017 |
| CN | 108052980 A | 5/2018 |
| CN | 109002859 A | 12/2018 |
| CN | 109799269 A | 5/2019 |
| CN | 109872060 A | 11/2019 |
| CN | 110517326 A | 11/2019 |

OTHER PUBLICATIONS

Abe et al., Classifier-independent feature selection on the basis of divergence criterion, Pattern Analytical Application 9:127-137 (2006).
Adebiyi et al., Rapid strain differentiation of *E. coli*-inoculated Urine using Olfactory-based Smart Sensors, 5th International Conference on Sensors Engineering and Electronics Instrumentation Advances (SEIA' 2019) (2019).
Agrawal et al., Intelligent Software Defined Atmospheric Effect Processing for 5th Generation (5G) Millimeter Wave (MMWave) Communication System, I.J. Wireless and Microwave Technologies 2:15-26 (2018).
Andrew et al., Multi-Stage Feature Selection Based Intelligent Classifier for Classification of Incipient Stage Fire in Building, Sensors 16:1-15 (2016).
Bahraminejad et al.,Real-Time Gas Identification by Analyzing the Transient Response of Capillary-Attached Conductive Gas Sensor, Sensors 10:5359-5377 (2010).
Blum et al., Selection of Relevant Features and Examples in Machine Learning, Artificial Intelligence 97:245-271 (1997).
Choi et al., The Wireless Electronic Noses and Mobile Devices Interoperation Based on Internet of Things Technology, Advanced Science and Technology Letters 120:149-152 (2015).
Gardner et al., Enhancing electronic nose performance by sensor selection using a new integer-based genetic algorithm approach, Sensors and Actuators B 106:114-121 (2005).
Gardner et al., Evaluating the Fairness of Predictive Student Models Through Slicing Analysis, International Learning Analytics & Knowledge Conference (LAK19) (2019).
Hall, Correlation-based Feature Selection for Machine Learning, Thesis for Department of Computer Science, The University of Waikato, Hamilton, New Zealand (1999).
Kumar et al., A Novel Method for Evaluation of Band Width of MEMS-Based Embedded Gas Sensor, American Journal of Materials Science 2(4):99-104 (2012).
Leidinger et al., Selective detection of hazardous VOCs for indoor air quality applications using a virtual gas sensor array, Journal of Sensors and Sensor Systems 3:253-263 (2014).
Muller et al., Limitations of High Dimension, Low Sample Size Principal Components for Gaussian Data, Journal of American Statistical Association (JASA) (2008).
Olfert et al., Acoustic method for measuring the sound speed of gases over small path lengths, Review of Scientific Instruments 78:05901.1-05902.8 (2007).
Wang et al., Metal Oxide Gas Sensors: Sensitivity and Influencing Factors, Sensors10:2088-2106 (2010).
Xiaobo et al., Vinegar Classification Based on Feature Extraction and Selection From Tin Oxide Gas Sensor Array Data, Sensors 3:101-109 (2003).
Yu et al., Feature Selection for High-Dimensional Data: A Fast Correlation-Based Filter Solution, Proceedings of the Twentieth International Conference on Machine Learning (ICML-2003) (2003).

* cited by examiner

SENSOR TUNING—SENSOR SPECIFIC SELECTION FOR IOT—ELECTRONIC NOSE APPLICATION USING GRADIENT BOOSTING DECISION TREES

TECHNICAL FIELD

The present invention relates generally to gas sensors and more specifically to a system and method for tuning gas sensors for a target application.

BACKGROUND OF THE INVENTION

An electronic nose is an intelligent sensing device that detects odors or flavors through the application of pattern recognition. A typical electronic nose includes an odor detection system, a sample delivery system, and a pattern recognition computing system. The odor detection system is an array of gas sensors; the sample delivery system delivers sample headspace into the detection system; and the pattern recognition system evaluates the components of an odor, analyzes its chemical make-up, and compares the components and chemical make-up of the odor to known aromas in order to identify the odor. Typical uses for an electronic nose include sensing environmental VOCs (Volatile Organic Compounds), sensing biological VOCs, and sensing VOCs emitted by food. Currently used electronic noses suffer from lack of selectivity for different applications. The present invention addresses this shortcoming.

SUMMARY OF THE INVENTION

The present invention provides systems and methods for tuning a gas sensor array and selecting the appropriate gas sensors in an array for a specific application.

In one embodiment, there is provided a system comprising: a sensor array; and a processor with at least one algorithm stored therein, wherein, raw data obtained from the sensor array are input into the processor to form an input set of extracted features, the at least one algorithm ranks the extracted features from the input set, wherein each extracted feature is given an importance value, and an importance score for each sensor of the sensor array is determined based upon the ranking of the extracted features for each sensor.

In another embodiment, there is provided a system comprising: a sensor array, and a processor with at least one algorithm stored therein, wherein, raw data obtained from the sensor array are input into the processor to form an input set of extracted features, wherein each extracted feature is given an importance value, the at least one algorithm ranks the extracted features from the input set, and a threshold value comprising an aggregate value of the extracted features is established, wherein individual sensors of the sensor array having extracted features ranked on or above the threshold value are suitable for a target application.

In a further embodiment, there is provided a system comprising: a sensor array; and a processor with at least one algorithm stored therein, wherein, raw data obtained from the sensor array are input into the processor to form an input set of extracted features, the at least one algorithm ranks extracted features from the input set, wherein each extracted feature is given an importance value, a threshold value comprising an aggregate value of the extracted features is established, and an importance score for each sensor of the sensor array is determined based upon the ranking of the extracted features for each sensor.

In one aspect, there is provided a method comprising the steps of: extracting features from an input set obtained from a sensor array; ranking the extracted features with at least one algorithm, wherein each extracted feature is given an importance value; calculating a threshold value for the ranked extracted features; calculating an importance score for individual sensors of the sensor array based upon the ranking of the extracted features; and selecting the individual sensors of the sensor array having an importance score on or above the threshold value for a target application.

In another aspect, there is provided a method comprising the steps of: preparing a sensor array for a target application and applying information to the sensor array to form an input set; extracting features from the input set and ranking the extracted features, wherein each extracted feature is given an importance value; calculating a threshold value for the extracted features; calculating an importance score for individual sensors of the sensor array based upon the ranking of the extracted features; and selecting the individual sensors for the target application that have an importance score above the threshold value.

In another embodiment and aspect, the threshold value refines the input set, and individual sensors having an importance score on or above the threshold value are selected for a target application.

In a further embodiment and aspect, the threshold value Thres is calculated according to Formula 1:

$$Thres = \frac{\sum fi}{\#feat} \quad \text{Formula 1}$$

wherein, fi is the importance value for each extracted feature from the input set, and #feat is the total number of extracted features from the input set.

In another embodiment and aspect, the importance score ImpSn of a single sensor in the sensor array is calculated according to Formula 2:

$$ImpSn = \frac{\sum fis}{\#feats} \quad \text{Formula 2}$$

wherein, fis is the importance value for each extracted feature for a single sensor, and #feats is the total number of extracted features for a single sensor.

In a further embodiment and aspect, the at least one algorithm comprises gradient boosting decision trees.

In another embodiment and aspect, the sensor array is comprised of a plurality of gas sensors.

In a further embodiment and aspect, the gas sensors measure volatile organic compounds (VOCS).

In another embodiment and aspect, the target application is selected from the group consisting of air quality analyses, air pollution analyses, water pollution analyses, soil analyses, lab test, medical tests, tests for allergens, breathalyzer tests, food and beverage expiration date analyses, food and beverage spoilage analyses, alcohol content analyses, product authenticity, and combinations thereof.

In a further embodiment and aspect, the product authenticity comprises identification of a crypto-currency digital footprint embedded in the product.

Additional embodiments and aspects of the invention will be provided, without limitation, in the detailed description of the invention that is set forth below.

DETAILED DESCRIPTION OF THE INVENTION

Set forth below is a description of what are currently believed to be preferred embodiments of the claimed invention. Any alternates or modifications in function, purpose, or structure are intended to be covered by the claims of this application. As used in this specification and the appended claims, the singular forms "a," "an," and "the" include plural referents unless the context clearly dictates otherwise. The terms "comprises" and/or "comprising," as used in this specification and the appended claims, specify the presence of stated features, integers, steps, operations, elements, and/or components, but do not preclude the presence or addition of one or more other features, integers, steps, operations, elements, components, and/or groups thereof.

As used herein, the term "importance value" or "fi" is meant to refer to the importance of features extracted from raw data obtained from a gas sensor array.

As used herein, the term "importance score" or "ImpSn" is meant to refer to the importance of each individual sensor of a sensor array, which is calculated according to the methods and systems described herein.

As used herein, the term "electronic nose" refers to the use of gas sensor arrays and pattern recognition systems to identify the specific components of an odor and analyze its chemical makeup to identify the odor. The electronic nose methods, systems, and applications described herein are meant to include Internet-of-Things (IoT)-based electronic noses; accordingly, as used herein, the term "electronic nose" in relation to a single device, a platform, or an application is meant to include IoT-electronic nose devices, platforms, and applications. With IoT-electronic noses, the electronic nose will include an RF (radio frequency) antenna for wireless communication with a receiving device, such as a computer or mobile device, where the user can view the gas sensing data and request the electronic nose to start and stop sensing data.

As used herein, the term "processor" refers to a computer processor or a microprocessor as those terms are known in the art. Within the context of the embodiments described herein, the purpose of the processor is to receive input from the gas sensors of the sensor arrays, carry out a computation, and provide appropriate output. The computations performed by the processor are the result of algorithms that are programmed into and stored within the processor.

Figure 1:
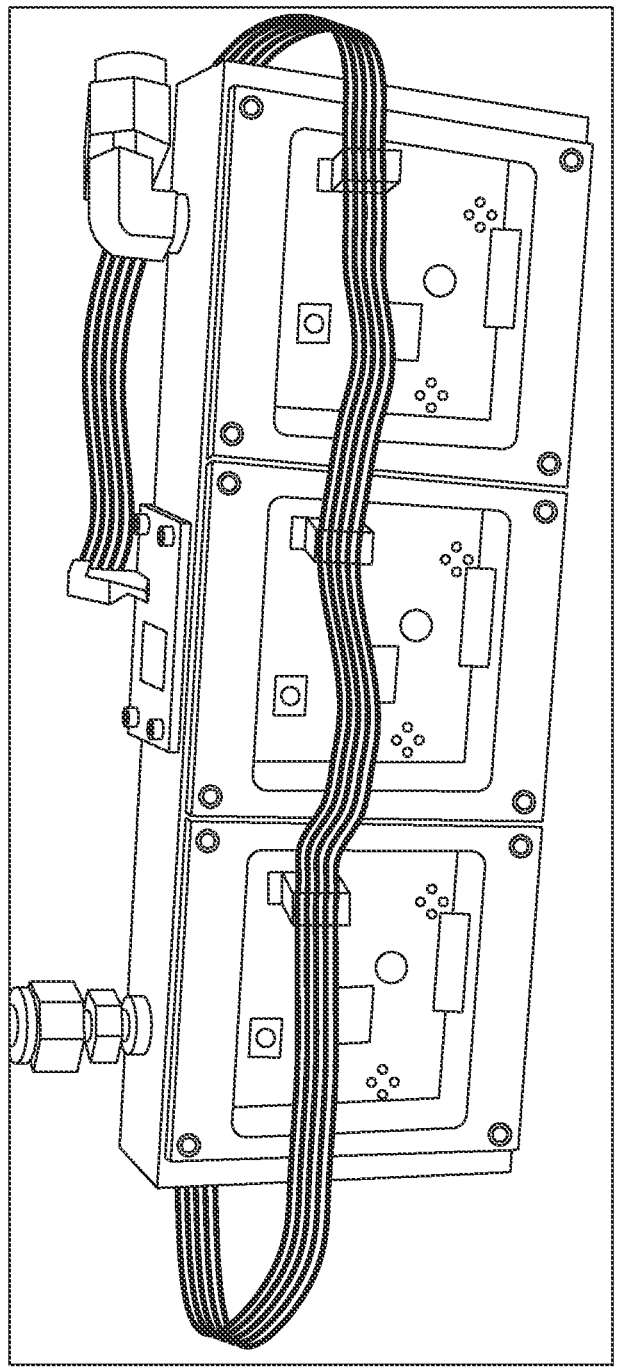
FIG. 1 is a photograph of an Electronic Volatile Analyzer (EVA) electronic nose platform equipped with six gas sensors (three of the sensors are shown, with the other three being on the opposite side of the platform).

FIG. 1 shows an Electronic Volatile Analyzer (EVA) electronic nose platform (also referred to herein as an "EVA platform") equipped with six gas sensors, each of which are mounted to modules integrated into the EVA platform. Only three of the six sensors are shown in FIG. 1; the other three are mounted to the modules on the opposite side of the EVA platform.

In order to increase the accuracy of an electronic nose for its target application, a gas sensor array must be tuned. The system and method described herein defines a specialized technique to use output of a decision tree-based system to optimize a combination of sensors in a sensor array that are best suited for a target application through proper classification.

Figure 2:
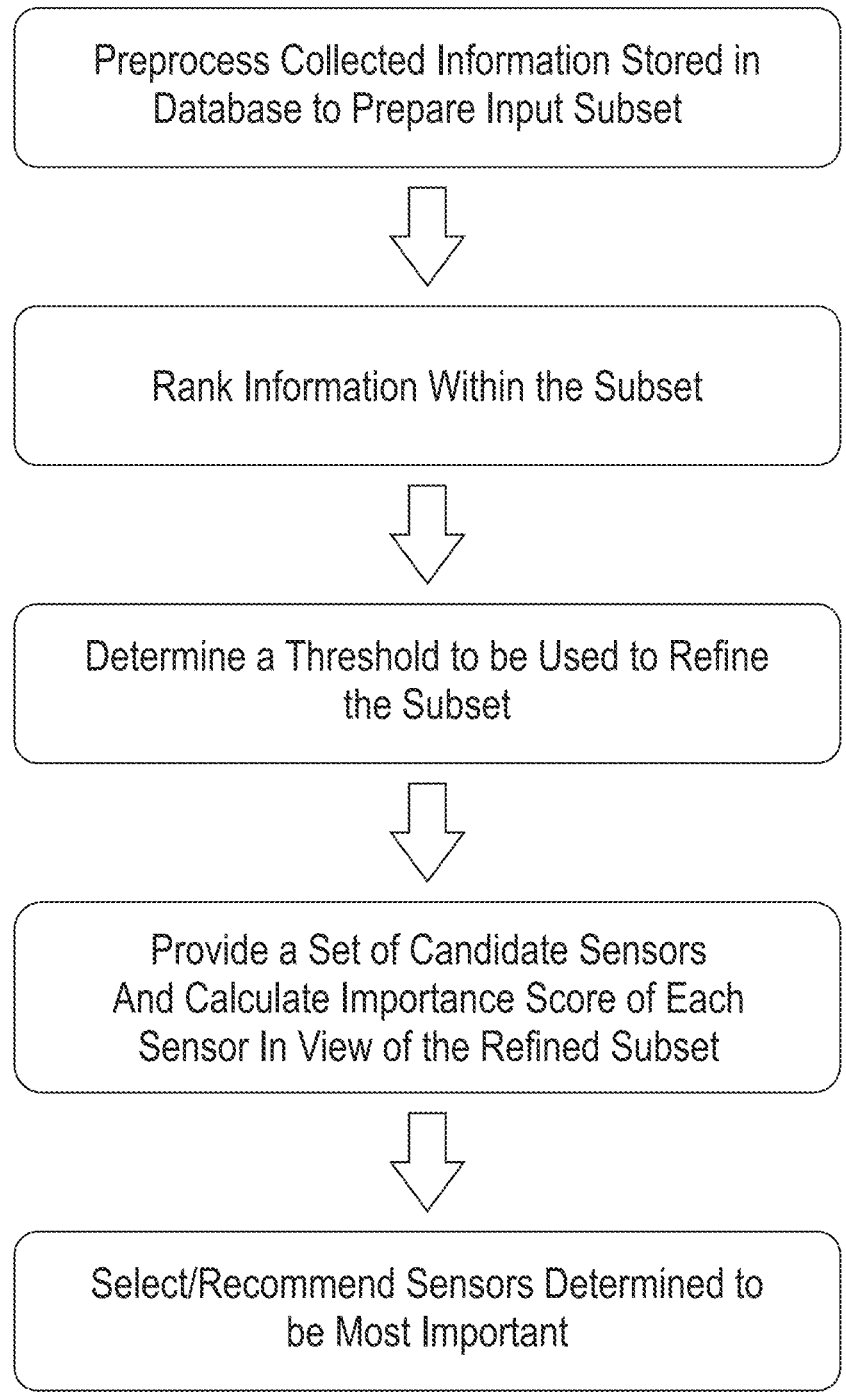
FIG. 2 is a flow chart showing the steps for tuning a sensor array as described herein.

FIG. 2 outlines the steps involved in the sensor selection system and method described herein. The first step in the sensor selection method is to pre-process and extract relevant features for samples from an array of sensors in order to prepare an input subset. The pre-processing and extraction may be carried out by any method known in the art. Some examples of feature extraction methods in machine learning application include, without limitation, linear discriminate analysis (LDA), principal component analysis (PCA), kernel PCA, multilinear PCA, artificial neural networking (ANN), independent component analysis, latent semantic analysis, partial least squares, multifactor dimensionality reduction, non-linear dimensionality reduction, multilinear subspace learning, semidefinite embedding, isomap, autoencoder, and combinations thereof. Following the pre-processing and extraction steps, the extracted features within the input set are ranked to form ranked subsets. The ranking involves constructing gradient boosting decision trees, initializing weights for all nodes, iterating through the nodes by calculating the weight reduction purity from a split, calculating the importance score for each tree based on performance measure (i.e., error function), and averaging the importance score across all trees.

To determine which sensor of a sensor array is most suitable for a particular application, two calculations are advantageously used. The first calculation is a threshold value Thres calculation according to Formula 1:

$$Thres = \frac{\sum fi}{\#feat} \qquad \text{Formula 1}$$

where Thres is a value that refines the ranking of the set of extracted features; fi is the importance of the individual extracted features in the ranked subset, and #feat is the total number of extracted features in the ranked subset. The threshold value calculation sets the lower limit by which the individual sensors in the sensor array will be judged for a target application. The second calculation is an importance score ImpSn calculation according to Formula 2:

$$ImpSn = \frac{\sum fis}{\#feats} \qquad \text{Formula 2}$$

where ImpSn is the importance score of a single sensor in the array (sensor n), fis is the importance value of the extracted features in sensor n, and #feats is the total number of extracted features in sensor n. The importance score calculation refines the ranking information of Formula 1 to be applicable to the individual sensors of a sensor array. Sensors with an importance score greater than or equal to the threshold value are selected for use in a sensor array for the target application. The sensors that fall under the threshold value are omitted from the sensor array.

Figure 3A:
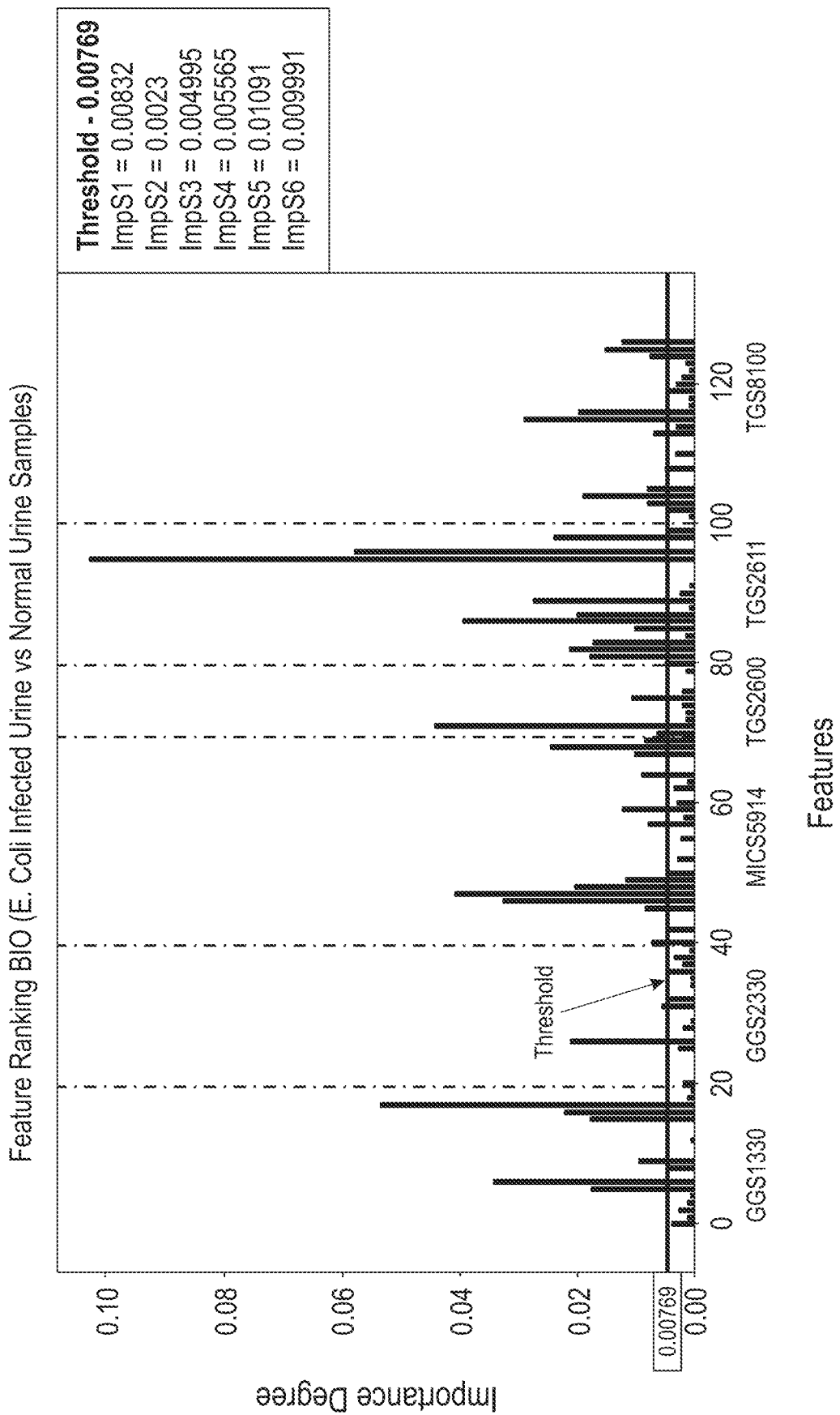
FIGS. 3A-3C show the results of applying the six-sensor electronic nose platform to biological (urine) samples for predicting a normal versus infected sample.
Figure 3B:
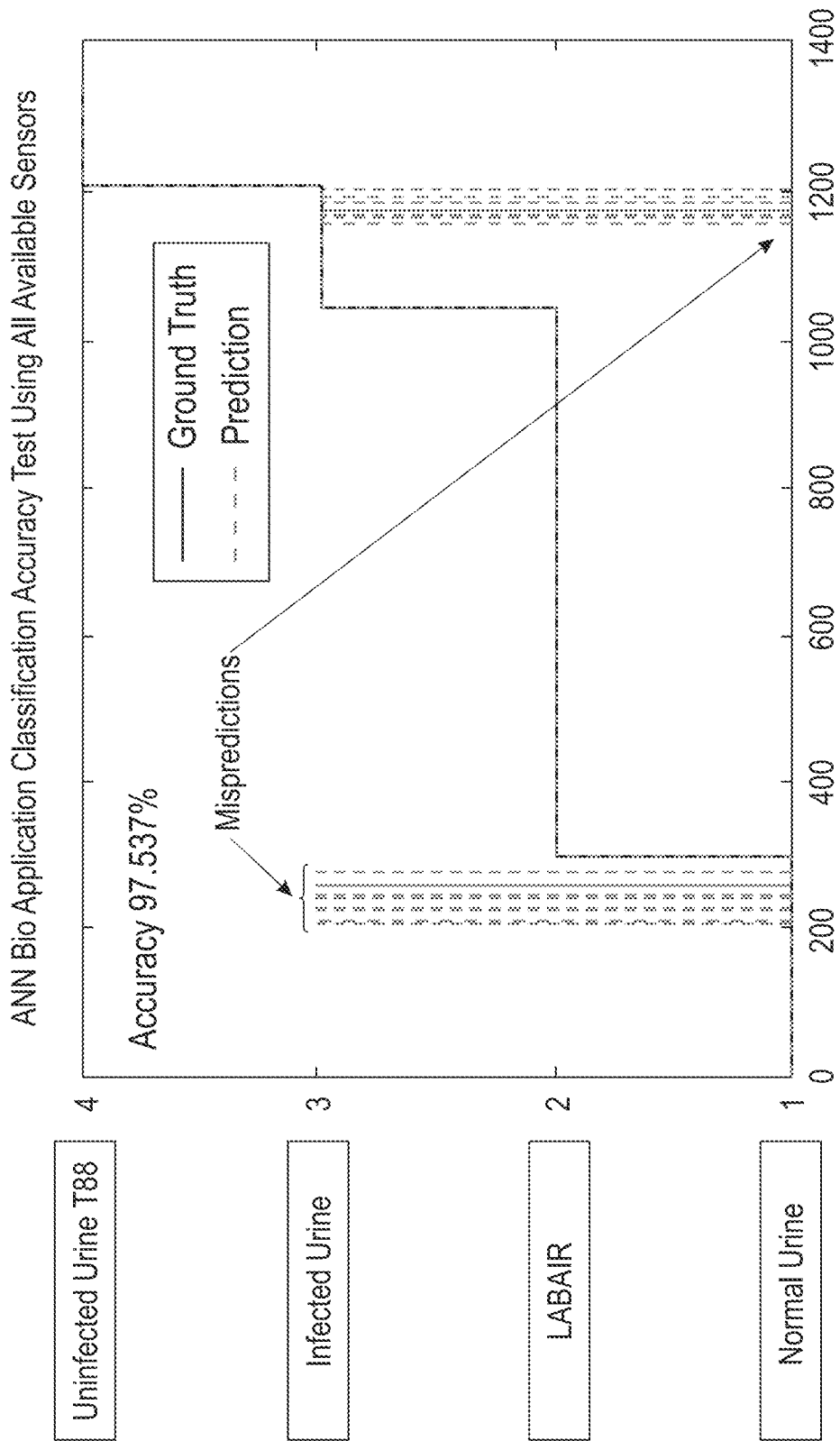
Figure 3C:
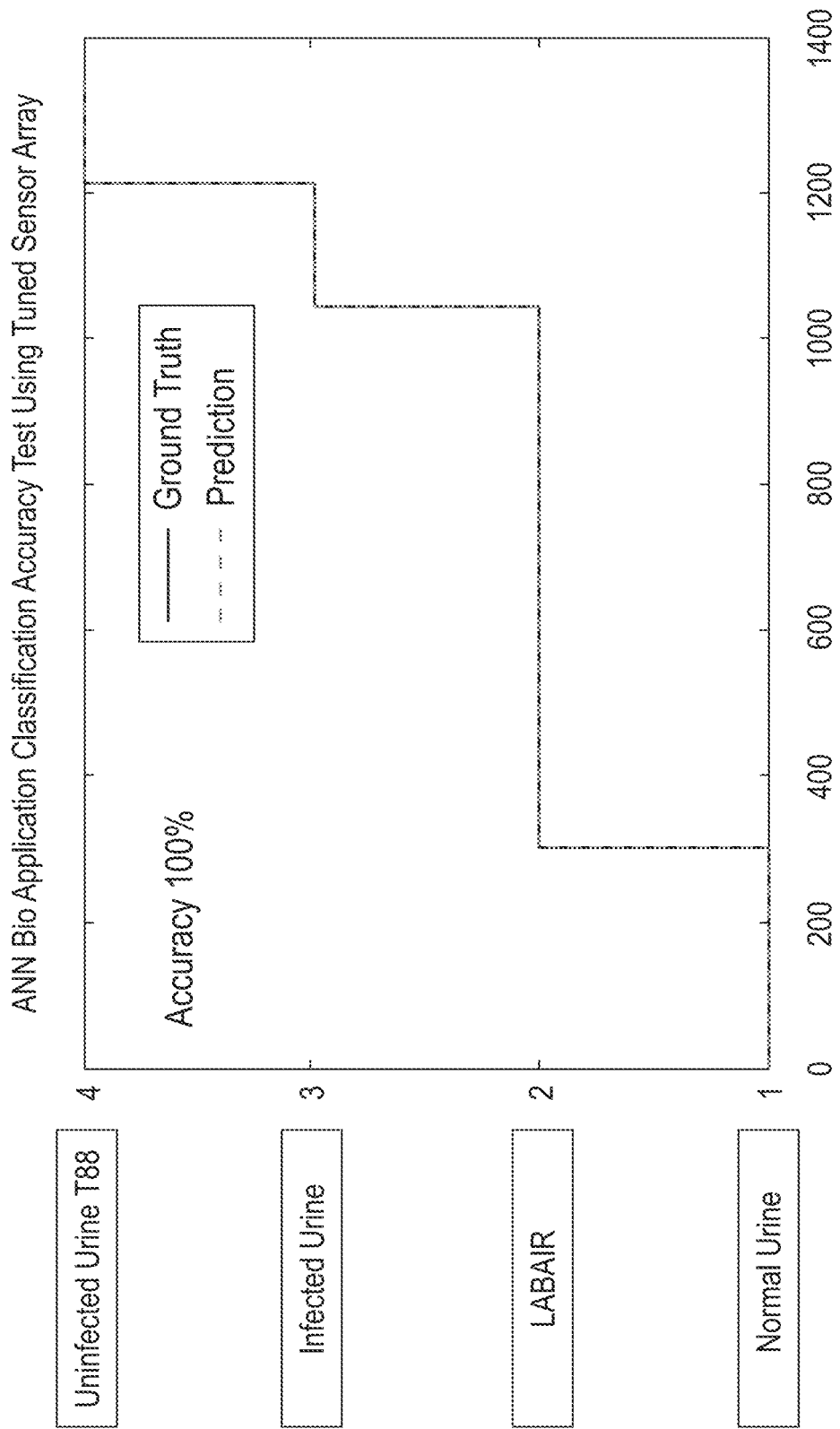

FIGS. 3A-3C show application of the threshold value and importance score to a six-sensor electronic nose platform (Example 1) used for a biological application (Example 2). As described in Example 2, six sensors recorded data on the following three biological samples: normal human serum (NHU); NHU infected with *Escherichia coli*; and NHU infected with *E. coli* and tryptic soy broth (TSB). As shown in FIG. 3A, each of the six sensors recorded feature values (y-axis) for their respective features (x-axis).

To reach the threshold value for the six sensors, the feature values of the 120 individual features of the six sensors are added together and divided by 120 to obtain a threshold value of 00.00769. The importance score for each sensor in the array is then determined using the importance score formula. For sensor GGS1330 (the first sensor in FIG. 3A), the importance score is 0.00832, which is calculated by aggregating all of the y-axis importance feature values and dividing that number by fifteen (the total number of features for GGS1330). Because the importance score of the GGS1330 sensor is above 0.00769, this sensor is a recommended sensor for the target biological application. When the importance score formula is applied to each of the six sensors in the array, three of the six sensors have importance scores above the threshold value; thus, three of the six sensors are recommended for the biological application (GGS1330, TGS2611, and TGS8100).

FIGS. 3B and 3C show the testing results of applying the six sensors versus the three recommended sensors to training and test samples of the NHU, the two *E. coli* samples, and lab air as a control. In FIG. 3B, which shows prediction results using all six sensors, approximately 80 of 300 NHU samples were misidentified as UTI samples, and approximately 50 of 200 UTI samples were misidentified as NHU samples. While the prediction accuracy of the tests in FIG. 3B came to 97.54%, this figure included 650 lab air samples, none of which were misidentified. When the three recommended samples were used for the biological application, the prediction accuracy of the testing was 100%, as is shown in FIG. 3C.

Figure 4A:
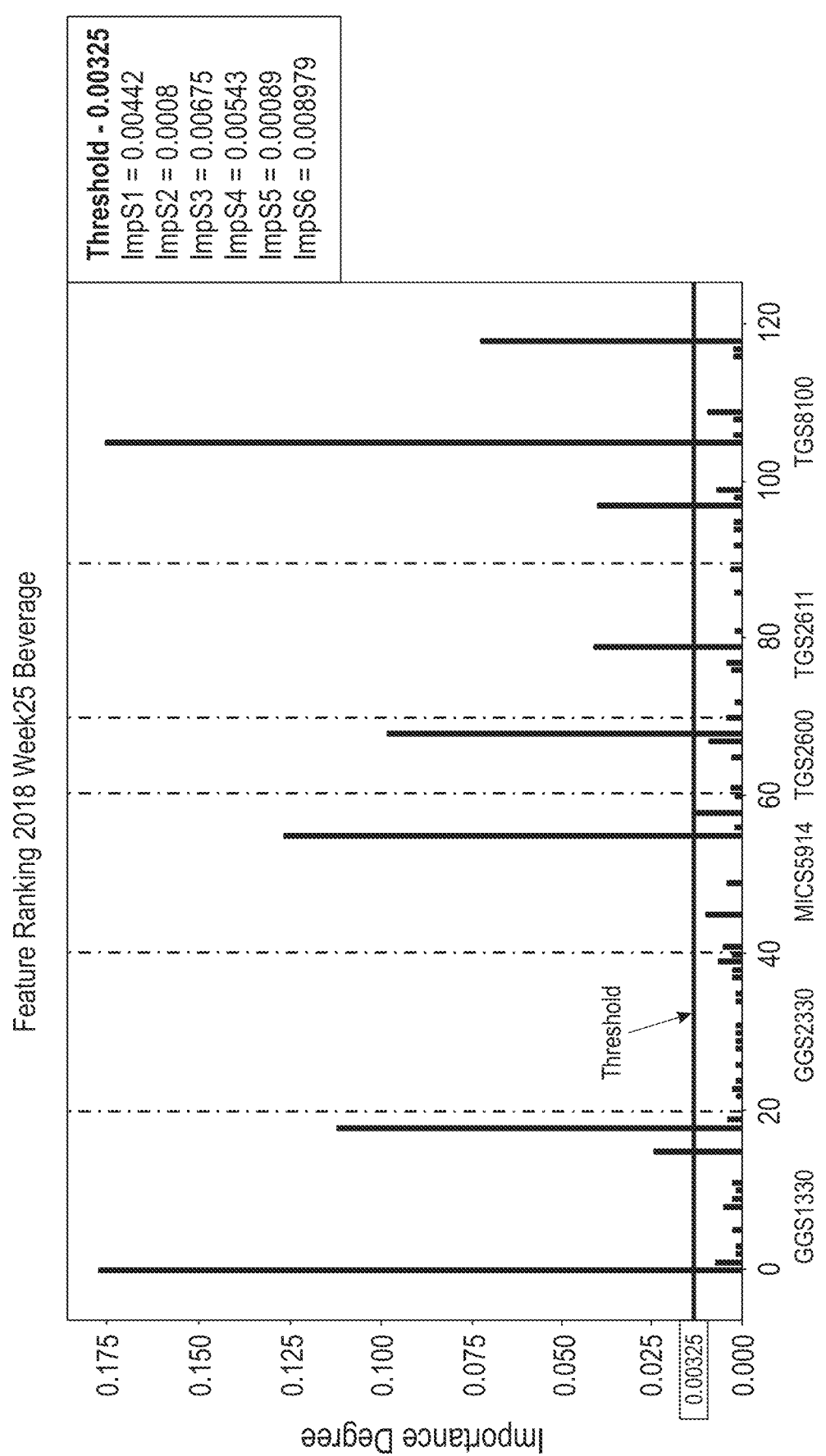
FIGS. 4A-4C show the results of applying the six-sensor electronic nose platform to five beverage samples and prediction results.
Figure 4B:
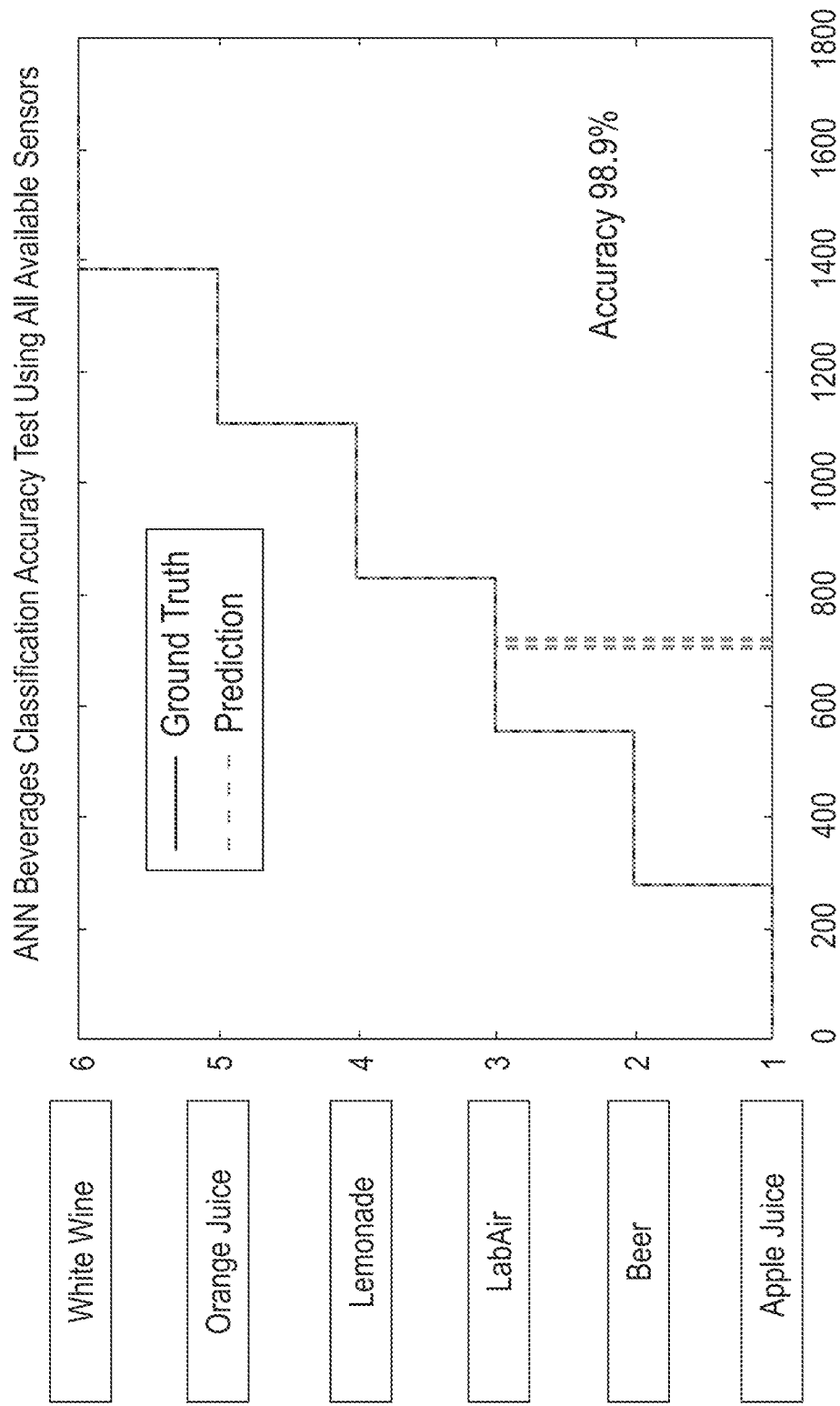
Figure 4C:
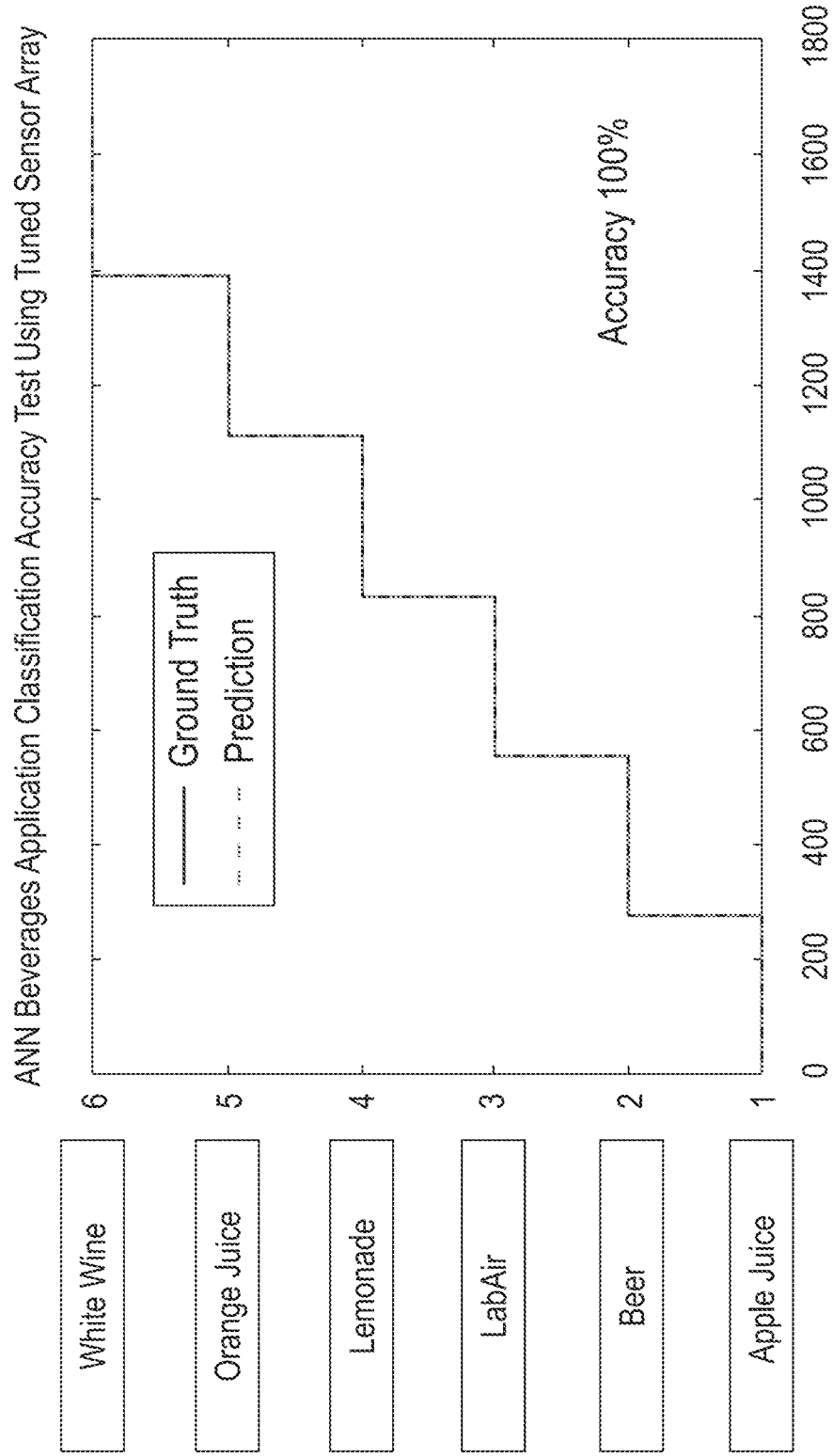

FIGS. 4A-4C show application of the threshold value and importance score for a beverage application (Example 3). The six sensors were tested on the following five beverages: apple juice, orange juice, lemonade, beer, and white wine. As shown in FIG. 4A, application of the threshold formula to the feature values resulted in a threshold value of 0.00325. Application of the importance formula resulted in four of the six sensors having an importance score above the threshold value; specifically, sensors GGS1330, MICS5914, TGS2600, and TGS8100.

FIGS. 4B and 4C show the testing results of applying the six sensors versus the four recommended sensors to training and test samples of the five beverages plus lab air as a control. When all six sensors were applied, the prediction accuracy was 98.9% with lab air being misidentified as apple juice in approximately 50 samples (FIG. 4B). When the four recommended sensors were used, the testing accuracy was 100% (FIG. 4C).

Figure 5A:
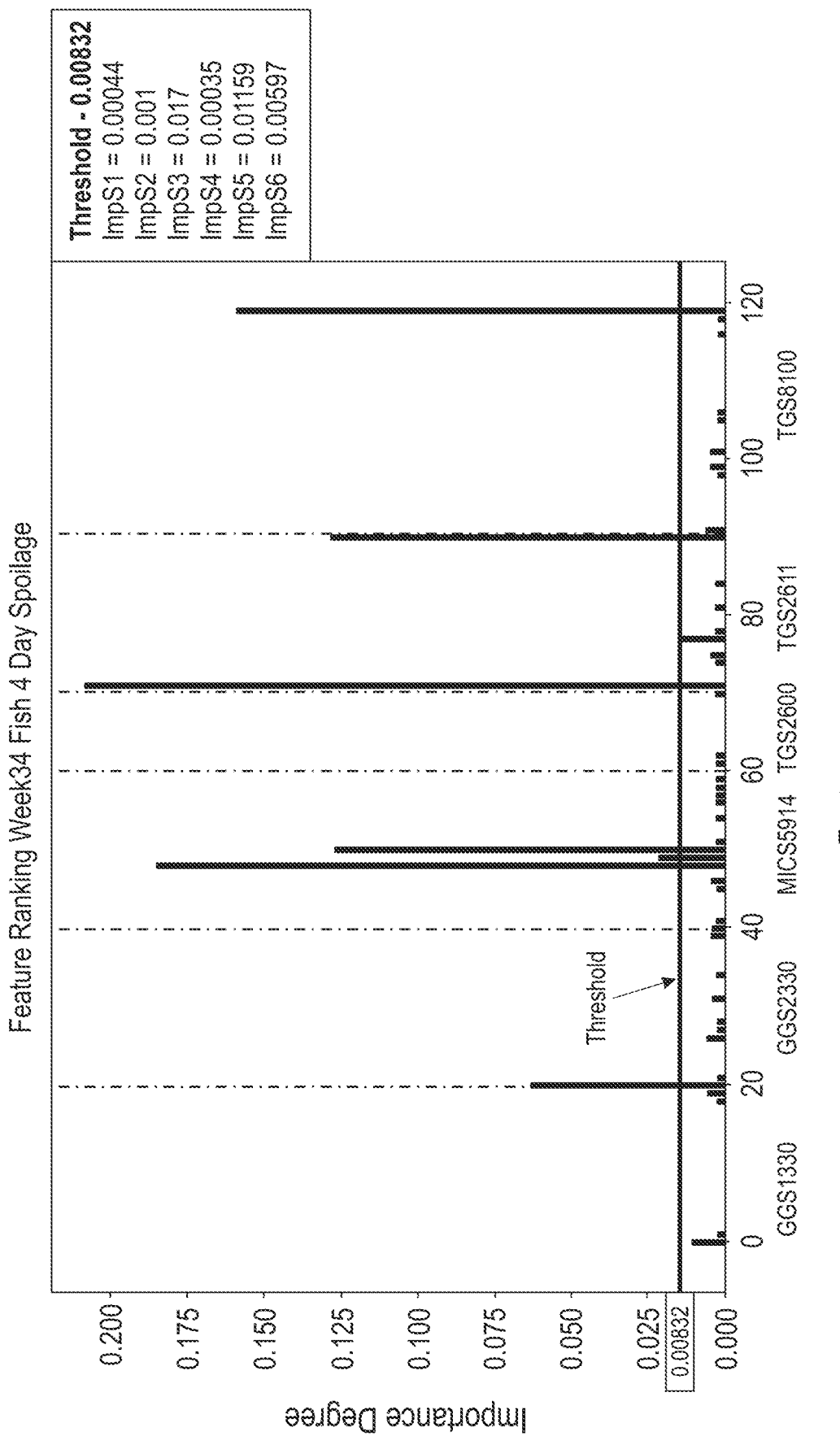
FIG. 5A-5C show the results of applying the six-sensor electronic nose platform to fish samples tested over the course of five days, from freshness (day 1) to spoilage (day 4).
Figure 5B:
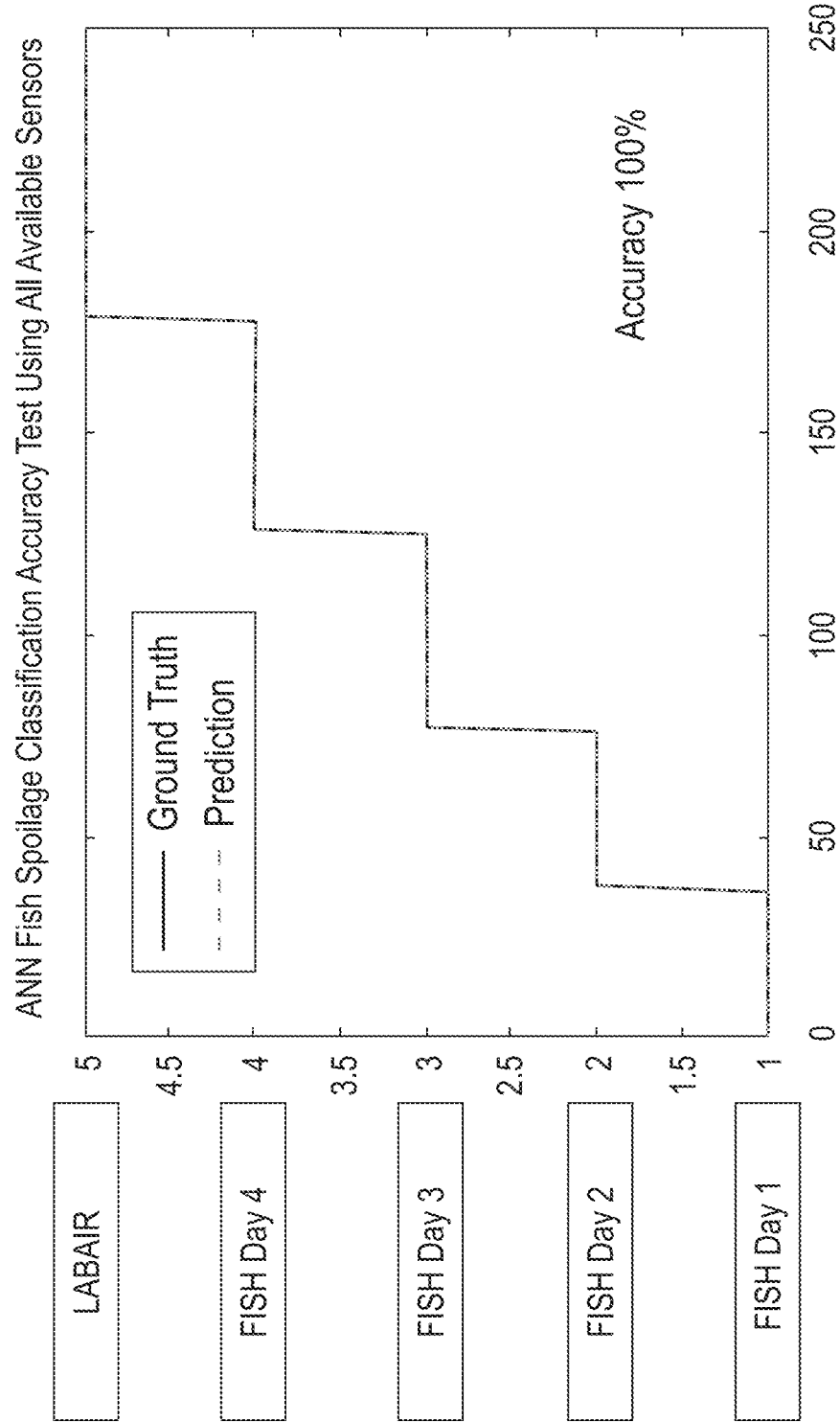
Figure 5C:
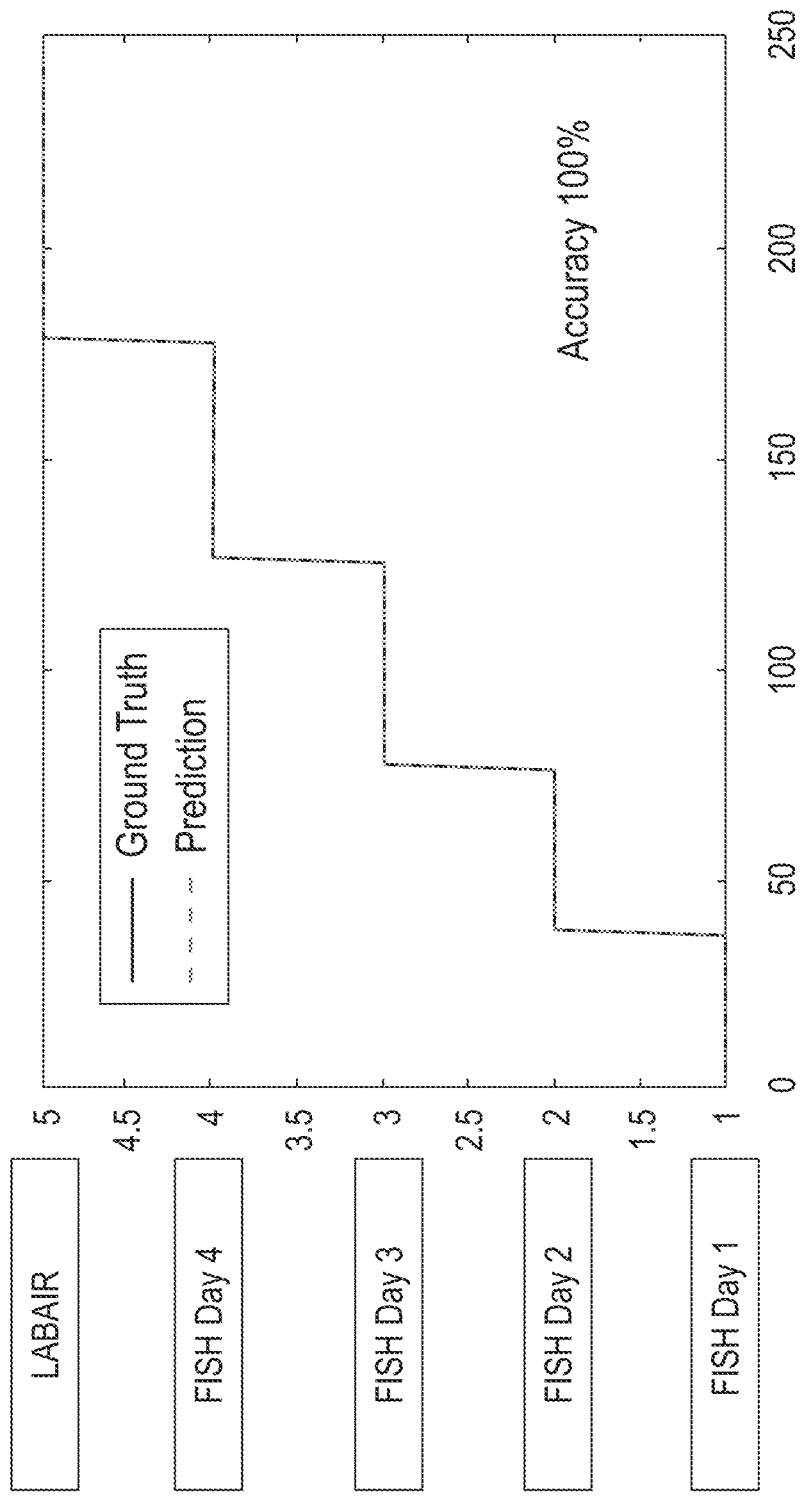

FIGS. 5A-5C show application of the sensor importance score for a food application (Example 4). Six sensors were tested on fish samples from day one (fresh fish) through day four (spoiled fish). As shown in FIG. 5A, application of the threshold formula to the feature values resulted in a threshold value of 0.00832. Application of the importance formula resulted in two of the six sensors having an importance score above the threshold value; specifically, sensors MICS5914 and TGS2611.

FIGS. 5B and 5C show the testing results of applying the six sensors versus the two recommended sensors to training and test samples of the fish samples from day 1 through day 4 plus lab air as a control. As shown in FIGS. 5B and 5C, the six-sensor array as well as the two recommended samples both yielded 100% accuracy in predicting the day of fish spoilage. The results of FIGS. 5B and 5C suggest that the non-recommended sensors did not add any advantage to the analysis and that the data from the two recommended sensors were sufficient for predicting fish freshness and spoilage.

The systems and methods described herein may be used for many electronic nose applications. For example, the system and method for fine tuning sensors may be used to fine tune gas sensors for detection of any VOCs. Examples of target applications that rely upon detection of VOCs include, without limitation, environmental applications (e.g., fire detection, air quality analyses, air pollution analyses, water pollution analyses, soil analyses); biological applications (e.g., lab test, medical tests, tests for allergens, breathalyzer tests); food and beverage applications (e.g., expiration date analyses, spoilage analyses, alcohol content analyses); and blockchain applications. With blockchain applications, crypto anchors (i.e., digital footprints) embedded in a wide range of VOC-emitting products may be identified by the EVA platform to ensure the authenticity of the products (Example 5). As previously noted, the electronic nose devices, platforms, and applications described herein may be operated as IoT-electronic nose devices, platforms, and applications.

The descriptions of the various embodiments of the present invention have been presented for purposes of illustration, but they are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

EXPERIMENTAL

The following examples are set forth to provide those of ordinary skill in the art with a complete disclosure of how to make and use the aspects and embodiments of the invention as set forth herein. While efforts have been made to ensure accuracy with respect to variables such as amounts, temperature, etc., experimental error and deviations should be taken into account. Unless indicated otherwise, parts are parts by weight, temperature is degrees centigrade, and pressure is at or near atmospheric. All components were obtained commercially unless otherwise indicated.

Example 1

Set Up of EVA Electronic Nose Platform

An EVA electronic nose platform (developed internally and shown in FIG. 1) was set up in a sealed chamber with six metal oxide gas (MOX) sensors each attached to six respective modules integrated within the EVA platform. The six MOX sensors were identified with the following names: GGS1330, GGS2330, MICS5914, TGS2600, TGS2611, and TGS8100. The EVA sensor platform was run with an open-source Python®-based software program (Python Software Foundation, Beaverton, Oreg., USA), which was developed internally to control the six modules of the EVA platform and the gas sensors attached thereto. A computer-controlled selector element (VICI® multipurpose actuator mobile control unit, Valco Instruments Co., Inc., Houston, Tex., USA) was connected to the sealed chamber containing the six MOX sensors. The selector element was used to collect vapors from the headspace of the individual vials that contained the samples for testing. A vacuum pump (Parker Model B.1F15E1.A12 VDC, Parker Hannifin, Hollis, N.H., USA) was placed downstream of the sealed chamber containing the six MOX sensors. The vacuum pump was regulated to generate a flow of 150 sccm through the sensor chamber, the selector element, and the selected vials (one vial was selected at a time). In operation, the vapors from the individual vials flowed from the vial headspace to the sensor chamber where the vapors interacted with the MOX sensor to trigger changes in the resistance of the sensors. The flow of the sample vapors through the system was measured with a Mass Flow Meter (ALICAT WHISPER™, Model MW-2SLPM-D/5M, Alicat Scientific, Tucson, Ariz., USA). In all experiments, a 20 mL vial with lab air was used as a control.

Example 2

The EVA Platform for Biological Applications

For a biological application, the EVA platform of Example 1 was tested with a sample of normal human urine (NHU), a sample of NHU inoculated with *Escherichia coli* (*E. coli*), and a sample of NHU inoculated with *E. coli* and tryptic soy broth (TSB), the two *E. coli* samples forming infected urine samples resembling a urinary tract infection (UTI). The NHU and the two UTI samples were individually placed in a 4 mL Wheaton septa top vials (DWK Life Sciences, Millville, N.J., USA). The three 4 mL sample vials plus the fourth 20 mL vial with the control lab air were attached to the selector element. Measurement data were acquired by connecting the three individual sample vials, in turn, to the sensor chamber via the selector element for a duration of 10 minutes during which time headspace measurements were taken from each vial. The three samples were incubated at 27° C. during measurements to aid in the evaporation of trapped volatiles. In between the data acquisitions, the MOX sensors were flushed with lab air for five minutes to promote sensor recovery by connecting the empty 20 mL vial to the sensor chamber and allowing the air flow to remove the vapors of the previous sample. By means of the selector element, each vial was repeatedly selected in a cyclic fashion over the course of an eight-hour collection period with an air flush in between the different vial collections. After the eight-hour collection period, the vials containing the biological samples were disposed of and replaced with fresh biological samples in fresh vials. Measurements were taken for a total of 34 weeks. The output of each MOX sensor consisted of the following data: sensor module ID, timestamp, sensor resistance, and heater voltage. The sensor output data were recorded in real-time for the duration of the experiment and stored in a separate text file for each sample exposure. The 34 week of collection data resulted in a total of 4459 raw data points.

The features of the raw data were extracted using artificial neural networking (ANN) to produce 20 extracted features per sensor for a total of 120 features. Gradient boosting decision trees were built to rank all of the extracted features from the six sensors using XGB Python® API open source software (Python Software Foundation, Beaverton, Oreg., USA). The feature extraction data after ranking for the biological measurements are shown in FIG. 3A. The threshold formula described herein was applied to the extracted feature data of FIG. 3A to yield a threshold value of 0.00769. The importance score formula described herein resulted in the following three sensors having an importance score above the threshold value: GGS1330, TGS2611, and TGS8100. The three selected sensors represented 50 features out of the total 120 features.

FIG. 3B shows training and test results for all six MOX sensors, and FIG. 3C shows training and test results for the three selected sensors that had an importance score above the threshold value. To obtain the training and test sets, 34-week collection data set were shuffled; 70% of the data were used as the training set and 30% of the data used as the test set. The training set consisted of 692 data points for the six sensors and 3121 data points for the three selected sensors. The test set consisted of 244 data points for the six sensors and 1337 data points for the three selected sensors. When the training and test set data were applied to the samples to test the prediction accuracy of the models, the six sensors yielded an accuracy of 97.5373% while the three selected sensors yielded an accuracy of 100%.

Example 3

The Eva Platform for Food/Beverage Applications

For a food/beverage application, the EVA platform of Example 1 was tested with the following five beverage samples each of which was placed in 5 mL Wheaton septa top vials: apple juice, orange juice, lemonade, beer, and white wine. The five 5 mL sample vials plus the fourth 20 mL vial with the control lab air were attached to the selector element. Training and test data were acquired by connecting the five individual sample vials, in turn, to the sensor chamber via the selector element for a duration of 10 minutes during which time headspace measurements were taken from each vial. The five samples were incubated at 27° C. during measurements to aid in the evaporation of trapped volatiles. In between the data acquisitions, the MOX sensors were flushed with lab air for five minutes to promote sensor recovery by connecting the empty 20 mL vial to the sensor chamber and allowing the air flow to remove the vapors of the previous sample. By means of the selector element, each vial was repeatedly selected in a cyclic fashion over the course of an eight-hour collection period with an air flush in between the different vial collections. After the eight-hour collection period, the vials containing the beverage samples were disposed of and replaced with fresh beverage samples in fresh vials. Measurements were taken for a total of 34 weeks. The output of each MOX sensor consisted of the following data: sensor module ID, timestamp, sensor resistance, and heater voltage. The sensor output data were recorded in real-time for the duration of the experiment and stored in a separate text file for each sample exposure. The 34 week of collection data resulted in a total of 1662 raw data points.

The features of the raw data were extracted using artificial neural networking (ANN) to produce 20 extracted features per sensor for a total of 120 features. Gradient boosting decision trees were built to rank all of the extracted features from the six sensors using XGB Python® API open source software. The feature extraction data after ranking for the biological measurements are shown in FIG. 4A. The threshold formula described herein was applied to the extracted feature data of FIG. 4A to yield a threshold value of 0.00325. The importance score formula described herein resulted in the following four sensors having an importance score above the threshold value: GGS1330, MICS5914, TGS2600, and TGS8100. The four selected sensors represented 80 features out of the total 120 features.

FIG. 4B shows training and test results using all six MOX sensors, and FIG. 4C shows training and test results for the four selected sensors that had an importance score above the threshold value. To obtain the training and test set data, the 34-week collection data were shuffled as described in Example 2 with 70% of the shuffled data used for the training set and the remaining 30% of the shuffled data used for the test set. The training set consisted of 2410 data points for both the six sensors the four selected sensors and the test set consisted of 1662 data points for both the six sensors and the four selected sensors. When the training and test set data were applied to samples to test the prediction accuracy of the models, the six sensors yielded an accuracy of 98.9% while the four selected sensors yielded an accuracy of 100%.

Example 4

The EVA Platform for Food Spoilage Applications

For a food spoilage application, the EVA platform of Example 1 was tested with a frozen salmon fish sample. To determine fish spoilage, the frozen fish was thawed and multiple samples of the fish were tested from day one (fresh) through day 4, with each individual sample of fish placed in 5 mL Wheaton septa top vials for testing. The 5 mL sample vials plus an additional 20 mL vial with the control lab air were attached to the selector element. Training and test data were acquired by connecting the sample vials, in turn, to the sensor chamber via the selector element for a duration of 10 minutes during which time headspace measurements were taken from each vial. The samples vials were incubated at 27° C. during measurements to aid in the evaporation of trapped volatiles. In between the data acquisitions, the MOX sensors were flushed with lab air for five minutes to promote sensor recovery by connecting the empty 20 mL vial to the sensor chamber and allowing the air flow to remove the vapors of the previous sample. By means of the selector element, each vial was repeatedly selected in a cyclic fashion over the course of an eight-hour collection period with an air flush in between the different vial collections. After the eight-hour collection period, the vials containing the fish samples were disposed of and replaced with fresh fish samples in fresh vials. Measurements were taken for a total of 34 weeks. The output of each MOX sensor consisted of the following data: sensor module ID, timestamp, sensor resistance, and heater voltage. The sensor output data were recorded in real-time for the duration of the experiment and stored in a separate text file for each sample exposure. The 34 week of collection data resulted in a total of 939 raw data points.

The features of the raw data were extracted using artificial neural networking (ANN) to produce 20 extracted features per sensor for a total of 120 features. Gradient boosting decision trees were built to rank all of the extracted features from the six sensors using XGB Python® API open source software. The feature extraction data after ranking for the biological measurements are shown in FIG. 5A. The threshold formula described herein was applied to the extracted feature data of FIG. 5A to yield a threshold value of 0.00325. The importance score formula described herein resulted in the following two sensors having an importance score above the threshold value: MICS5914 and TGS2611. The two selected sensors represented 40 features out of the total 120 features.

FIG. 5B shows training and test results using for all six MOX sensors and FIG. 5C shows training and test results for the two selected sensors that had an importance score above the threshold value. To obtain the training and test set data, the 34-week collection data were shuffled as described in Examples 2 and 3 with 70% of the shuffled data used for training and 30% of the shuffled data used for testing. The training set consisted of 692 data points for both the six sensors and the two selected sensors and the test set consisted of 244 data points for both the six sensors and the two selected sensors. When the training and test set data were applied to samples to test the prediction accuracy of the models, both the six sensors and the two selected sensors yielded an accuracy of 100%.

Example 5

EVA Platform for Blockchain Applications

For blockchain applications, the EVA platform is used to confirm the authenticity of food, beverage, or agricultural products that have been marked with a crypto-anchor that emits a digital footprint. For testing, a sample of a VOC-emitting food, beverage, or agricultural products is prepared in vials for testing using the EVA platform and testing procedures as described in Examples 2-4. The software running the EVA platform is programmed to identify the presence of the digital footprint emitted from the crypto-anchor. Products that test positive for the crypto-anchor digital footprint are deemed authentic while products that test negative for the crypto-anchor digital footprint are deemed to be counterfeit.

We claim:

1. A system comprising:
a sensor array, and
a processor with at least one algorithm stored therein, wherein,
raw data obtained from the sensor array are input into the processor to form an input set of extracted features, wherein a threshold value Thres calculated according to Formula 1 refines the input set:

$$Thres = \frac{\sum fi}{\#feat} \quad \text{Formula 1}$$

wherein,
fi is the importance value for each extracted feature from the input set, and
feat is the total number of extracted features from the input set;
the at least one algorithm ranks the extracted features from the input set, wherein each extracted feature is given an importance value; and
an importance score for each sensor of the sensor array is determined based upon the ranking of the extracted features for each sensor.

2. The method of claim 1, wherein individual sensors having an importance score on or above the threshold value are selected for a target application.

3. The system of claim 2, wherein the target application is selected from the group consisting of air quality analyses, air pollution analyses, water pollution analyses, soil analyses, lab test, medical tests, tests for allergens, breathalyzer tests, food and beverage expiration date analyses, food and beverage spoilage analyses, alcohol content analyses, product authenticity, and combinations thereof.

4. The system of claim 3, wherein the product authenticity comprises identification of a crypto-currency digital footprint embedded in the product.

5. The system of claim 1, wherein the importance score ImpSn of a single sensor in the sensor array is calculated according to Formula 2:

$$ImpSn = \frac{\sum fis}{\#feats} \qquad \text{Formula 2}$$

wherein,
fis is the importance value for each extracted feature for a single sensor, and
feats is the total number of extracted features for a single sensor.

6. The system of claim 1, wherein the at least one algorithm comprises gradient boosting decision trees.

7. The system of claim 1, wherein the sensor array is comprised of a plurality of gas sensors and the gas sensors measure volatile organic compounds (VOCs).

8. A system comprising:
a sensor array, and
a processor with at least one algorithm stored therein, wherein,
raw data obtained from the sensor array are input into the processor to form an input set of extracted features, wherein each extracted feature is given an importance value;
the at least one algorithm ranks the extracted features from the input set; and
a threshold value Thres comprising an aggregate value of the extracted features is calculated according to Formula 1:

$$Thres = \frac{\sum fi}{\#feat} \qquad \text{Formula 1}$$

wherein,
fi is the importance value for each extracted feature from the input set, and
feat is the total number of extracted features from the input set,
wherein individual sensors of the sensor array having extracted features ranked on or above the threshold value are suitable for a target application.

9. The system of claim 8, wherein the extracted features of the individual sensors are ranked in relation to the threshold value with an importance score ImpSn that is calculated according to Formula 2:

$$ImpSn = \frac{\sum fis}{\#feats} \qquad \text{Formula 2}$$

wherein,
fis is the importance value for each extracted feature for a single sensor,
feats is the total number of extracted features in for a single sensor.

10. The system of claim 9, wherein an individual sensor with an importance score on or above the threshold level is suitable for the target application.

11. A system comprising:
a sensor array, and
a processor with at least one algorithm stored therein, wherein,
raw data obtained from the sensor array are input into the processor to form an input set of extracted features;
the at least one algorithm ranks extracted features from the input set, wherein each extracted feature is given an importance value;
a threshold value Thres comprising an aggregate value of the extracted features is; and
an importance score for each sensor of the sensor array is calculated according to Formula 2:

$$ImpSn = \frac{\sum fis}{\#feats} \qquad \text{Formula 2}$$

wherein,
fis is the importance value for each extracted feature for a single sensor, and
feats is the total number of features in a single sensor.

12. The system of claim 11, wherein individual sensors of the sensor array having an importance score on or above the threshold value are suitable for a target application.

13. The system of claim 11, wherein the threshold value Thres is calculated according to Formula 1:

$$Thres = \frac{\sum fi}{\#feat} \qquad \text{Formula 1}$$

wherein,
fi is the importance value for each extracted feature from the input set, and
feat is the total number of extracted features in the input set.

14. A method comprising the steps of:
extracting features from an input set obtained from a sensor array;
ranking the extracted features with at least one algorithm, wherein each extracted feature is given an importance value;
calculating a threshold value Thres for the ranked extracted features according to Formula 1:

$$Thres = \frac{\sum fi}{\#feat} \qquad \text{Formula 1}$$

wherein,
fi is the importance value for each extracted feature from the input set, and
feat is the total number of extracted features from the input set;

calculating an importance score for individual sensors of the sensor array based upon the ranking of the extracted features; and selecting the individual sensors of the sensor array having an importance score on or above the threshold value for a target application.

15. The method of claim 14, wherein the importance score is calculated according to Formula 2:

$$ImpSn = \frac{\sum fis}{\#feats} \qquad \text{Formula 2}$$

wherein,
fis is the importance value for each extracted feature for a single sensor, and
feats is the total number of extracted features extracted for a single sensor.

16. The method of claim 14, wherein the feature values are ranked with an algorithm comprising gradient boosting decision trees.

17. The method of claim 14, wherein the sensor array is comprised of a plurality of gas sensors and the gas sensors measure volatile organic compounds (VOCs).

18. The method of claim 14, wherein the target application is selected from the group consisting of air quality analyses, air pollution analyses, water pollution analyses, soil analyses, lab test, medical tests, tests for allergens, breathalyzer tests, food and beverage expiration date analyses, food and beverage spoilage analyses, alcohol content analyses, product authenticity, and combinations thereof.

19. The method of claim 18, wherein the product authenticity comprises identification of a crypto-currency digital footprint embedded in the product.

20. A method comprising the steps of:
preparing a sensor array for a target application and applying information to the sensor array to form an input set;
extracting features from the input set and ranking the extracted features, wherein each extracted feature is given an importance value;
calculating a threshold value Thres for the extracted features according to Formula 1:

$$Thres = \frac{\sum fi}{\#feat} \qquad \text{Formula 1}$$

wherein
fi is the importance value for each extracted feature from the input set, and
feat is the total number of extracted features from the input set;
calculating an importance score for individual sensors of the sensor array based upon the ranking of the extracted features; and
selecting the individual sensors for the target application that have an importance score above the threshold value.

21. The method of claim 20, wherein the importance score ImpSn is calculated according to Formula 2:

$$ImpSn = \frac{\sum fis}{\#feats} \qquad \text{Formula 2}$$

wherein,
fis is the importance value for each extracted feature for a single sensor, and
feats is the total number of extracted features in a single sensor.

22. The method of claim 20, wherein the extracted features are ranked with an algorithm comprising gradient boosting decision trees.

23. The method of claim 20, wherein the sensor array is comprised of a plurality of gas sensors and the gas sensors measure volatile organic compounds (VOCs).

24. The method of claim 20, wherein the target application is selected from the group consisting of air quality analyses, air pollution analyses, water pollution analyses, soil analyses, lab tests, medical tests, tests for allergens, breathalyzer tests, food and beverage expiration date analyses, food and beverage spoilage analyses, alcohol content analyses, product authenticity, and combinations thereof.

25. The method of claim 24, wherein the product authenticity comprises identification of a crypto-currency digital footprint embedded in the product.

* * * * *